United States Patent [19]

Buss

[11] Patent Number: 4,517,306

[45] Date of Patent: May 14, 1985

[54] COMPOSITION AND A METHOD FOR ITS USE IN DEHYDROCYCLIZATION OF ALKANES

[75] Inventor: Waldeen C. Buss, Kensington, Calif.

[73] Assignee: Chevron Research Company, San Francisco, Calif.

[21] Appl. No.: 567,834

[22] Filed: Jan. 3, 1984

Related U.S. Application Data

[62] Division of Ser. No. 344,571, Feb. 1, 1982, Pat. No. 4,447,316.

[51] Int. Cl.$^3$ .............................................. B01J 29/12
[52] U.S. Cl. ......................................... 502/74; 502/66
[58] Field of Search .................................. 502/66, 74

[56] References Cited

U.S. PATENT DOCUMENTS

| | | | |
|---|---|---|---|
| 3,403,108 | 9/1968 | Leftin et al. | 502/74 |
| 3,640,819 | 2/1972 | Walkins | 502/74 X |
| 3,783,123 | 1/1974 | Young | 208/111 |
| 3,794,600 | 2/1974 | Schutt | 502/74 |
| 4,448,891 | 5/1984 | Cohen | 502/74 |

FOREIGN PATENT DOCUMENTS

| | | | |
|---|---|---|---|
| 618765 | 4/1961 | Canada | 502/74 |
| 62253 | 5/1977 | Japan | 502/74 |

*Primary Examiner*—Carl F. Dees
*Attorney, Agent, or Firm*—S. R. LaPaglia; W. K. Turner; Ernest A. Schaal

[57] ABSTRACT

A new catalyst is disclosed which is useful for dehydrocyclizing alkanes. This catalyst contains a type L zeolite, a Group VIII metal, and an alkaline earth metal. This catalyst has been reduced in a hydrogen atmosphere at a temperature of from 480° C. to 620° C.

7 Claims, No Drawings

COMPOSITION AND A METHOD FOR ITS USE IN DEHYDROCYCLIZATION OF ALKANES

This is a division of application Ser. No. 344,571, filed Feb. 1, 1982, now U.S. Pat. No. 4,447,316.

BACKGROUND OF THE INVENTION

The invention relates to a new catalyst and a method using that catalyst in reforming hydrocarbons, more particularly hydrocarbons comprising paraffins containing at least 6 carbon atoms, to form the corresponding aromatic hydrocarbons.

Catalytic reforming is well known in the petroleum industry and refers to the treatment of naphtha fractions to improve the octane rating. The more important hydrocarbon reactions occurring during reforming operation employing catalysts comprising dehydrogenation-promoting metal components include dehydrogenation of 6-ring naphthenes and dehydroisomerization of alkyl-cyclopentanes to aromatics, dehydrocyclization of paraffins to aromatics, isomerization of normal paraffins to isoparaffins, dealkylation of alkylbenzenes, and hydrocracking of relatively long-chained paraffins. Hydrocracking reactions which produce high yields of light gaseous hydrocarbons, e.g., methane and ethane, are to be particularly avoided during reforming as this decreases the yield of gasoline boiling products. Furthermore, since hydrocracking is an exothermic process, as contrasted to reforming which, in general, is endothermic, hydrocracking reactions which result in the production of high yields of light gaseous products are generally accompanied by severe temperature excursions which can result in temperature runaways in a reforming operation.

Dehydrocyclization is one of the main reactions in the reforming process. The conventional methods of performing these dehydrocyclization reactions are based on the use of catalysts comprising a noble metal on a carrier. Known catalysts of this kind are based on alumina carrying 0.2% to 0.8% by weight of platinum and preferably a second auxiliary metal.

The possibility of using carriers other than alumina has also been studied and it was proposed to use certain molecular sieves such as X and Y zeolites, which appeared suitable provided that the reactant and product molecules were sufficiently small to pass through the pores of the zeolite. However, catalysts based upon these molecular sieves have not been commercially successful.

In the conventional method of carrying out the aforementioned dehydrocyclization, hydrocarbons to be converted are passed over the catalyst, in the presence of hydrogen, at temperatures of 430° C. to 550° C. and pressures of 100 to 500 psig. Part of the hydrocarbons are converted into aromatic hydrocarbons, and the reaction is accompanied by isomerization and cracking reactions which also convert the paraffins into isoparaffins and lighter hydrocarbons.

The rate of conversion of the hydrocarbons into aromatic hydrocarbons varies with the reaction conditions and the nature of the catalyst.

The catalysts hitherto used have given satisfactory results with heavy paraffins, but less satisfactory results with $C_6$–$C_8$ paraffins, particularly $C_6$ paraffins. Catalysts based on a type L zeolite are more selective with regard to the dehydrocyclization reaction; can be used to improve the rate of conversion to aromatic hydrocarbons without requiring higher temperatures and lower pressures, which usually have a considerable adverse effect on the stability of the catalyst; and produce excellent results with $C_6$–$C_8$ paraffins, but run length and regenerability are problems and satisfactory regeneration procedures are not known.

In one method of dehydrocyclizing aliphatic hydrocarbons, hydrocarbons are contacted in the presence of hydrogen at a temperature of 430° C. to 550° C. with a catalyst consisting essentially of a type L zeolite having exchangeable cations of which at least 90% are alkali metal ions selected from the group consisting of ions of sodium, lithium, potassium, rubidium and cesium and containing at least one metal selected from the group which consists of metals of Group VIII of the Periodic Table of Elements, tin and germanium, said metal or metals including at least one metal from Group VIII of said Periodic Table having a dehydrogenating effect, so as to convert at least part of the feedstock into aromatic hydrocarbons.

A particularly advantageous embodiment of this method is a platinum/alkali metal/type L zeolite catalyst because of its excellent activity and selectivity for converting hexanes and heptanes to aromatics, but run length and regenerability remain a problem.

SUMMARY OF THE INVENTION

The present invention overcomes the deficiencies of the prior art by using a catalyst comprising a type L zeolite, an alkaline earth metal and a Group VIII metal, which has been reduced in a hydrogen atmosphere at a temperature of from 480° C. to 620° C., to reform hydrocarbons. This process gives vastly superior selectivity for converting alkanes to aromatics than shown in prior art processes. This process also gives satisfactory run length and regenerability. The hydrocarbons are contacted with a catalyst comprising a type L zeolite; at least one Group VIII metal (preferably platinum); and an alkaline earth metal selected from the group consisting of barium, strontium and calcium (preferably barium). Prior to contacting the hydrocarbons with the zeolite, the zeolite is reduced in a hydrogen atmosphere at a temperature of from 480° C. to 620° C., preferably from 530° C. to 620° C.

Preferably, the type L zeolite contains from 0.1% to 5% by weight platinum and 0.1% to 35% by weight barium. The hydrocarbons are contacted with the barium-exchanged type zeolite at a temperature of from 400° C. to 600° C. (preferably 450° C. to 550° C.); an LHSV of from 0.3 to 5; a pressure of from 1 atmosphere to 500 psig (preferably from 50 to 200 psig); and an $H_2$/HC ratio of from 1:1 to 10:1 (preferably from 2:1 to 6:1).

DESCRIPTION OF THE PREFERRED EMBODIMENTS

In its broadest aspect, the present invention involves a catalyst comprising a type L zeolite, an alkaline earth metal and a Group VIII metal, which has been reduced in a hydrogen atmosphere at a temperature of from 480° C. to 620° C., and its use in reforming hydrocarbons, in particular, the dehydrocyclization of alkanes at a high selectivity.

The term "selectivity" as used in the present invention is defined as the percentage of moles of paraffin converted to aromatics relative to moles converted to aromatics and cracked products, $$\text{i.e., Selectivity} = \frac{100 \times \text{moles of paraffins converted to aromatics}}{\text{moles of paraffins converted to aromatics and cracked products}}$$

Isomerization reactions are not considered in determining selectivity.

The term "selectivity for n-hexane" as used in the present invention is defined as the percentage of moles of n-hexane converted to aromatics relative to moles converted to aromatics and cracked products.

The selectivity for converting paraffins to aromatics is a measure of the efficiency of the process in converting paraffins to the desired and valuable products: aromatics and hydrogen, as opposed to the less desirable products of hydrocracking.

Highly selective catalysts produce more hydrogen than less selective catalysts because hydrogen is produced when paraffins are converted to aromatics and hydrogen is consumed when paraffins are converted to cracked products. Increasing the selectivity of the process increases the amount of hydrogen produced (more aromatization) and decreases the amount of hydrogen consumed (less cracking).

Another advantage of using highly selective catalysts is that the hydrogen produced by highly selective catalysts is purer than that produced by less selective catalysts. This higher purity results because more hydrogen is produced, while less low boiling hydrocarbons (cracked products) are produced. The purity of hydrogen produced in reforming is critical if, as is usually the case in an integrated refinery, the hydrogen produced is utilized in processes such as hydrotreating and hydrocracking, which require at least certain minimum partial pressures of hydrogen. If the purity becomes too low, the hydrogen can no longer be used for this purpose and must be used in a less valuable way, for example as fuel gas.

In the method according to the invention, the feed hydrocarbons preferably comprise nonaromatic hydrocarbons containing at least 6 carbon atoms. Preferably, the feedstock is substantially free of sulfur, nitrogen, metals, and other known poisons for reforming catalysts.

The dehydrocyclization is carried out in the presence of hydrogen at a pressure adjusted so as to favor the reaction thermodynamically and limit undesirable hydrocracking reactions by kinetic means. The pressures used preferably vary from 1 atmosphere to 500 psig, more preferably from 50 to 200 psig, the molar ratio of hydrogen to hydrocarbons preferably being from 1:1 to 10:1, more preferably from 2:1 to 6:1.

In the temperature range of from 400° C. to 600° C., the dehydrocyclization reaction occurs with acceptable speed and selectivity.

If the operating temperature is below 400° C., the reaction speed is insufficient and consequently the yield is too low for industrial purposes. When the operating temperature is above 600° C., interfering secondary reactions such as hydrocracking and coking occur, and substantially reduce the yield. It is not advisable, therefore, to exceed the temperature of 600° C.

The preferred temperature range (450° C. to 550° C.) is that in which the process is optimum with regard to activity, selectivity and the stability of the catalyst.

The liquid hourly space velocity of the hydrocarbons is preferably between 0.3 and 5.

The catalyst according to the invention is a type L zeolite charged with one or more dehydrogenating constituents.

Type L zeolites are synthetic zeolites. A theoretical formula is $M_{9/n}[(AlO_2)_9(SiO_2)_{27}]$ in which M is a cation having the valency n.

The real formula may vary without changing the crystalline structure; for example, the mole ratio of silicon to aluminum (Si/Al) may vary from 1.5 to 3.5.

A more complete description of these zeolites is given, e.g., in U.S. Pat. No. 3,216,789 which, more particularly, gives a conventional description of these zeolites with respect to their X-ray diffraction spectrum. U.S. Pat. No. 3,216,789 is hereby incorporated by reference to show a method of forming a type L zeolite useful in the present invention.

The hydrocarbon sorption pores are channels parallel to the cylinder axis and approximately 7 to 8 Angstroms in diameter.

Type L zeolites are conventionally synthesized largely in the potassium form, i.e., in the theoretical formula given previously, most of the M cations are potassium. The M cations are exchangeable, so that a given type L zeolite, e.g., a type L zeolite in the potassium form, can be used to obtain type L zeolites containing other cations, by subjecting the type L zeolite to ion exchange treatment in an aqueous solution of appropriate salts. However, it is difficult to exchange all of the original cations, e.g., potassium, since some exchangeable cations in the zeolite are in sites which are difficult for the reagents to reach.

An essential element of the present invention is the presence of an alkaline earth metal in the type L zeolite. That alkaline earth metal must be either barium, strontium or calcium, preferably barium. The alkaline earth metal can be incorporated into the zeolite by synthesis, impregnation or ion exchange. Barium is preferred to the other alkaline earths because it results in a somewhat less acidic catalyst. Strong acidity is undesirable in the catalyst because it promotes cracking, resulting in lower selectivity.

In one embodiment, at least part of the alkali metal is exchanged with barium, using techniques known for ion exchange of zeolites. This involves contacting the zeolite with a solution containing excess $Ba^{++}$ ions. The barium should constitute from 0.1% to 35% of the weight of the zeolite.

The catalysts according to the invention are charged with one or more Group VIII metals, e.g., nickel, ruthenium, rhodium, palladium, iridium or platinum.

The preferred Group VIII metals are iridium and particularly platinum, which are more selective with regard to dehydrocyclization and are also more stable under the dehydrocyclization treatment conditions than other Group VIII metals.

The preferred percentage of platinum in the catalyst is between 0.1% and 5%, the lower limit corresponding to minimum catalyst activity and the upper limit to maximum activity.

Group VIII metals are introduced into the L zeolite by synthesis, impregnation or exchange in an aqueous solution of appropriate salt. When it is desired to introduce two Group VIII metals into the zeolite, the operation may be carried out simultaneously or sequentially.

By way of example, platinum can be introduced by impregnating the zeolite with an aqueous solution of tetrammineplatinum (II) nitrate, chloroplatinic acid, chloroplatinuous acid, dinitrodiamino-platinum or tetrammineplatinum (II) chloride. In an ion exchange process, platinum can be introduced by using cationic platinum complexes such as tetrammineplatinum (II) nitrate.

An inorganic oxide is used as a carrier to bind the type L zeolite containing the Group VIII metal and alkaline earth metal. The carrier can be a natural or a synthetically produced inorganic oxide or combination of inorganic oxides. Typical inorganic oxide supports which can be used include clays, alumina, and silica, in which acidic sites are preferably exchanged by cations which do not impart strong acidity (such as Na, K, Rb, Cs, Ca, Sr, or Ba).

The catalysts can be employed in any of the conventional types of equipment known to the art. It may be employed in the form of pills, pellets, granules, broken fragments, or various special shapes, disposed as a fixed bed within a reaction zone, and the charging stock may be passed therethrough in the liquid, vapor, or mixed phase, and in either upward or downward flow. Alternatively, it may be prepared in a suitable form for use in moving beds, or in fluidized-solid processes, in which the charging stock is passed upward through a turbulent bed of finely divided catalyst. The reaction products from any of the foregoing processes are separated from the catalyst, vented to atmospheric pressure, and fractionated to recover the various components thereof.

After the desired metal or metals have been introduced, the catalyst is treated in air at about 260° C. and then reduced in hydrogen at temperatures of from 200° C. to 700° C., preferably 530° C. to 620 C.

At this stage it is ready for use in the dehydrocyclization process. In some cases however, for example when the metal or metals have been introduced by an ion exchange process, it is preferable to eliminate any residual acidity of the zeolite by treating the catalyst with an aqueous solution of a salt of a suitable alkali or alkaline earth element in order to neutralize any hydrogen ions formed during the reduction of metal ions by hydrogen.

In order to obtain optimum selectivity, temperature should be adjusted so that reaction rate is appreciable, but conversion is less than 98%, as excessive temperature and excess reaction can have an adverse affect on selectivity. Pressure should also be adjusted within a proper range. Too high a pressure will place a thermodynamic (equilibrium) limit on the desired reaction, especially for hexane aromatization, and too low a pressure may result in coking and deactivation.

Although the primary benefit of this invention is in improving the selectivity for conversion of paraffins (especially $C_6$-$C_8$ paraffins) to aromatics, it is also surprisingly found that the selectivity for conversion of methylcyclopentane to aromatics is excellent. This reaction, which on conventional reforming catalysts based on chlorided alumina involves an acid catalyzed isomerization step, occurs on the catalyst of this invention with as good or better selectivity than on the chlorided alumina based catalysts of the prior art. Thus, the present invention can also be used to catalyze the conversion of stocks high in 5-membered-ring naphthenes to aromatics.

Another advantage of this invention is that the catalyst of the present invention is more stable than prior art zeolitic catalysts. Stability of the catalyst, or resistance to deactivation, determines its useful run length. Longer run lengths result in less down time and expense in regenerating or replacing the catalyst charge.

EXAMPLES

The invention will be further illustrated by the following examples which set forth a particularly advantageous method and composition embodiments. While the examples are provided to illustrate the present invention, they are not intended to limit it.

EXAMPLE I

An Arabian Light straight run which had been hydrofined to remove sulfur, oxygen and nitrogen was reformed at 100 psig, 2 LHSV, and $6H_2/HC$ by three different processes. The feed contained 80.2 v% paraffins, 16.7 v% naphthenes, and 3.1 v% aromatics, and it contained 21.8 v% $C_5$, 52.9 v% $C_6$, 21.3 v% $C_7$, and 3.2 v% $C_8$.

In the first process, the Arabian Light straight run was reformed at 499° C. using a platinum-rhenium-alumina catalyst prepared by the process disclosed in U.S. Pat. No. 3,415,737.

In the second process, the Arabian Light straight run was reformed at 493° C. using a platinum-potassium-type L zeolite catalyst formed by: (1) impregnating a potassium-type L zeolite with 0.8% platinum using tetrammineplatinum (II) nitrate; (2) drying the catalyst; and (3) calcining the catalyst at 260° C.

In the third process, the process of the present invention, the Arabian Light straight run was reformed at 493° C. using a platinum-barium-type L zeolite catalyst formed by: (1) ion exchanging a potassium-type L zeolite with a sufficient volume of 0.17 molar barium nitrate solution to contain an excess of barium compared to the ion exchange capacity of the zeolite; (2) drying the resulting barium-exchanged type L zeolite catalyst; (3) calcining the catalyst at 590° C.; (4) impregnating the catalyst with 0.8% platinum using tetrammineplatinum (II) nitrate; (5) drying the catalyst; (6) calcining the catalyst at 260° C.; and (7) reducing the catalyst in hydrogen at 480° C. for 1 hour.

The results of these three runs are shown in Table I.

TABLE I

|  | Feed | 499° C. Pt/Re/ Alumina | 493° C. Pt/K/L | 493° C. Pt/Ba/L |
|---|---|---|---|---|
| $C_1$ Wt % Fd |  | 2.8 | 5.5 | 3.6 |
| $C_2$ |  | 6.6 | 2.5 | 1.3 |
| $C_3$ |  | 9.3 | 3.2 | 1.5 |
| $iC_4$ | 0.1 | 5.8 | 0.9 | 0.5 |
| $NC_4$ | 0.5 | 6.8 | 3.8 | 2.4 |
| $iC_5$ | 5.1 | 13.6 | 6.7 | 5.6 |
| $NC_5$ | 11.3 | 9.8 | 12.6 | 12.6 |
| $C_6$ + P + N | 81.3 | 13.4 | 7.8 | 9.3 |
| Benzene | 1.5 | 15.1 | 40.6 | 43.8 |
| $C_7$ + Aromatics | .8 | 15.8 | 12.7 | 15.0 |
| $C_5$ + LV % Yield |  | 63 | 69.9 | 74.4 |
| Hydrogen, SCF/B |  | 470 | 1660 | 2050 |
| Selectivity, Mole % $C_6$ + P → Aromatics |  | 20 | 72 | 87 |

This series of runs shows that the use of a platinum-barium-type L zeolite catalyst in reforming gives a selectivity for converting hexanes to benzene markedly superior to that of the prior art. Notice that associated with this superior selectivity is an increase in hydrogen gas production, which can be used in other processes. Notice also that the hydrogen purity is higher for the Pt/Ba/L run since more hydrogen is produced and less $C_1$ plus $C_2$ are produced.

EXAMPLE II

A second series of runs was made using n-hexane as feed. All runs in this series were made at 490° C., 100 psig, 3 LHSV and 3H$_2$/HC.

In the first run, a platinum-potassium-type L zeolite was used which had been prepared by the procedures shown in the second process of Example I.

In the second run, a platinum-barium-type L zeolite was used which had been prepared by the procedures shown in the third process of Example I except that the barium nitrate solution was 0.3 molar instead of 0.17 molar. The results of these runs are given below in Table II.

TABLE II

|  | Conversion | | Selectivity for n-hexane | |
|---|---|---|---|---|
|  | 5 Hrs. | 20 Hrs. | 5 Hrs. | 20 Hrs. |
| Pt/K/L | 70 | 59 | 76 | 79 |
| Pt/Ba/L | 85 | 85 | 89 | 92 |

Thus, in operation, the incorporation of barium into type L zeolite causes a dramatic improvement in selectivity for n-hexane. Notice that the stability of the platinum-barium-type L zeolite is excellent. Afte 20 hours, there was no drop in conversion when platinum-barium-type L zeolite catalyst was used.

EXAMPLE III

A third series of runs was made to show the effects of reduction temperature. The feed used was the same as in Example I. Run conditions were 490° C., 100 psig, 2.0 LHSV, 6.0H$_2$/HC.

The catalyst used in the first two runs was a Pt/Ba/K/L made as in the third process of Example I, except that the barium exchange was done three times with a 1 molar barium nitrate solution; this gave only a small increase in barium content.

The catalyst in the last two runs was a Pt/K/L made as in the second process of Example I.

Results obtained after 3 hours of operation are shown in Table III.

TABLE III

|  | Reduction Conditions | Aromatics Mole % Feed | Selectivity Mole % |
|---|---|---|---|
| Pt/Ba/K/L | 490° C., 1 Hr. | 59 | 78 |
| Pt/Ba/K/L | 620° C., 20 Hrs. | 60 | 89 |
| Pt/K/L | 490° C., 1 Hr. | 55 | 66 |
| Pt/K/L | 620° C., 20 Hrs. | 23 | 23 |

The results show a large and surprising difference in the effect of prereduction on the two catalysts. The selectivity of the barium-containing catalyst was substantially improved, while the selectivity of the catalyst without barium was very substantially decreased.

While the present invention has been described with reference to specific embodiments, this application is intended to cover those various changes and substitutions which may be made by those skilled in the art without departing from the spirit and scope of the appended claims.

I claim:
1. A composition comprising:
   (a) a type L zeolite;
   (b) at least one Group VIII metal; and
   (c) an alkalline earth metal selected from the group consisting of barium, strontium and calcium, wherein said compositon is reduced in a hydrogen atmosphere at a temperature of from 480° C. to 620° C.
2. A composition according to claim 1 wherein said composition is reduced in a hydrogen atmosphere at a temperature of from 530° C. to 620° C.
3. A composition according to claim 2 wherein said alkaline earth metal is barium and wherein said Group VIII metal is platinum.
4. A composition according to claim 3 wherein said type L zeolite has from 0.1% to 5% by weight platinum and 0.1% to 35% by weight barium.
5. A composition consisting essentially of:
   (a) a type L zeolite;
   (b) an inorganic oxide binder;
   (c) platinum; and
   (d) barium; wherein said composition is reduced in a hydrogen atmosphere at a temperature of from 480° C. to 620° C.
6. A composition according to claim 5 wherein said composition is reduced in a hydrogen atmosphere at a temperature of from 530° C. to 620° C.
7. A composition according to claim 6 wherein said type L zeolite has from 0.1% to 5% by weight platinum and 0.1% to 35% by weight barium.

* * * * *

UNITED STATES PATENT AND TRADEMARK OFFICE
CERTIFICATE OF CORRECTION

PATENT NO. : 4,517,306
DATED : May 14, 1985
INVENTOR(S) : WALDEEN C. BUSS

It is certified that error appears in the above-identified patent and that said Letters Patent are hereby corrected as shown below:

Col. 6, line 40, "480°C for 1 hour" should read --480°C to 500°C for 1 hour--

Signed and Sealed this

Twelfth Day of November 1985

[SEAL]

Attest:

Attesting Officer

DONALD J. QUIGG

Commissioner of Patents and Trademarks